(12) United States Patent
Junio

(10) Patent No.: US 12,156,705 B2
(45) Date of Patent: Dec. 3, 2024

(54) SYSTEMS AND METHODS FOR GENERATING MULTIPLE REGISTRATIONS

(71) Applicant: Mazor Robotics Ltd., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 316 days.

(21) Appl. No.: 17/697,799

(22) Filed: Mar. 17, 2022

(65) Prior Publication Data

US 2022/0354584 A1 Nov. 10, 2022

Related U.S. Application Data

(60) Provisional application No. 63/184,526, filed on May 5, 2021.

(51) Int. Cl.
*A61B 34/20* (2016.01)
*A61B 34/32* (2016.01)
*A61B 90/00* (2016.01)

(52) U.S. Cl.
CPC ............. *A61B 34/20* (2016.02); *A61B 34/32* (2016.02); *A61B 90/36* (2016.02); *A61B 90/39* (2016.02); *A61B 2034/2065* (2016.02); *A61B 2034/2068* (2016.02); *A61B 2090/363* (2016.02); *A61B 2090/3966* (2016.02)

(58) Field of Classification Search
CPC .. A61B 2017/00119; A61B 2034/2051; A61B 2034/2055; A61B 2034/2065; A61B 2034/2068; A61B 2090/363; A61B 2090/371; A61B 2090/3735; A61B 2090/374; A61B 2090/376; A61B 2090/3762; A61B 2090/378; A61B 2090/3966; A61B 34/20; A61B 34/30; A61B 34/32; A61B 90/20; A61B 90/36; A61B 90/39
See application file for complete search history.

(56) References Cited

U.S. PATENT DOCUMENTS

| | | | |
|---|---|---|---|
| 8,311,611 B2 | 11/2012 | Csavoy et al. | |
| 10,751,127 B2 | 8/2020 | Dace et al. | |
| 2008/0119725 A1* | 5/2008 | Lloyd | A61B 90/36 600/424 |
| 2009/0177081 A1 | 7/2009 | Joskowicz et al. | |

(Continued)

FOREIGN PATENT DOCUMENTS

EP 3662857 6/2020

OTHER PUBLICATIONS

International Search Report and Written Opinion for International (PCT) Patent Application No. PCT/IL2022/050448, dated Aug. 18, 2022, 14 pages.

*Primary Examiner* — Amelie R Davis
(74) *Attorney, Agent, or Firm* — Sheridan Ross P.C.

(57) ABSTRACT

Systems and methods for generating multiple registrations is provided. An image depicting a portion of a patient's anatomy and a tracking device affixed to an accurate robot may be received. A first registration of a patient coordinate space to a robotic coordinate space may be generated based on the image. A second registration of the patient coordinate space to a navigation coordinate space based at least in part on a position of second markers on the tracking device detected by a navigation system may be generated. The first registration and the second registration may be independent of each other.

17 Claims, 5 Drawing Sheets

(56) References Cited

U.S. PATENT DOCUMENTS

| | | | |
|---|---|---|---|
| 2014/0206990 A1* | 7/2014 | Epstein | A61B 90/37 |
| | | | 600/587 |
| 2018/0221098 A1 | 8/2018 | Forsyth et al. | |
| 2018/0263714 A1 | 9/2018 | Kostrzewski et al. | |
| 2020/0222127 A1 | 7/2020 | Snyder et al. | |

* cited by examiner

SYSTEMS AND METHODS FOR GENERATING MULTIPLE REGISTRATIONS

CROSS REFERENCE TO RELATED APPLICATIONS

This application claims the benefit of U.S. Provisional Application No. 63/184,526, filed on May 5, 2021, and entitled "Systems and Methods for Generating Multiple Registrations", which application is incorporated herein by reference in its entirety.

FIELD

The present technology generally relates to registration for a surgical procedure, and relates more particularly to generating multiple registrations for a surgical procedure.

BACKGROUND

Navigation systems may guide a surgeon or other medical provider in carrying out a surgical procedure, or may complete one or more surgical procedures. The navigation system may use a registration process to correlate a patient to the navigation system. Imaging may be used to aid in the registration process.

SUMMARY

Example aspects of the present disclosure include:

A method for dual registration according to at least one embodiment of the present disclosure comprises receiving an image depicting a portion of a patient's anatomy and a tracking device affixed to an accurate robot, the tracking device having first markers visible in the image and second markers visible to a navigation system; generating a first registration of a patient coordinate space to a robotic coordinate space based on the image; generating a second registration of the patient coordinate space to a navigation coordinate space based at least in part on a position of the second markers detected by the navigation system; wherein the first registration and the second registration are independent of each other.

Any of the aspects herein, wherein the first registration is also based on information about a pose of the accurate robot in the image.

Any of the aspects herein, wherein the image is an X-ray image.

Any of the aspects herein, further comprising generating a third registration of the robotic coordinate space to the navigation coordinate space based on the first registration.

Any of the aspects herein, further comprising generating a fourth registration of the navigation coordinate space to the robotic coordinate space based on the second registration.

Any of the aspects herein, further comprising comparing the third registration to the fourth registration to yield an error determination.

Any of the aspects herein, further comprising verifying an accuracy of the first registration or the second registration by causing the accurate robot or a navigated tool, respectively, to contact a known point relative to the patient's anatomy.

Any of the aspects herein, wherein the known point relative to the patient's anatomy is a point on an anatomical feature of the patient's anatomy.

Any of the aspects herein, further comprising: comparing a first tool pose of a navigated tool with a predetermined tool pose, the first tool pose detected by the navigation system while the navigated tool is at least partially supported by the accurate robot; and generating an alert when the first tool pose does not match the predetermined tool pose.

Any of the aspects herein, further comprising: defining a single point in space using the first registration to yield a first position; defining the single point in space using the second registration to yield a second position; quantifying a difference between the first position and the second position; and comparing the difference to a predetermined threshold.

A system for generating registrations according to at least one embodiment of the present disclosure comprises a tracking device affixed to an accurate robot, the tracking device comprising first markers visible to an imaging device and second markers visible to a navigation system; a processor; and a memory storing data for processing by the processor, the data, when processed, causing the processor to: register a patient coordinate system to a robotic coordinate system, based on an image depicting an anatomical portion of a patient and the tracking device, to yield a first registration; and register the patient coordinate system to a navigation coordinate system, based at least in part on a position of the second markers detected by the navigation system, to yield a second registration; wherein the first registration and the second registration are independent of each other.

Any of the aspects herein, wherein the memory stores further data for processing by the processor that, when processed, causes the processor to: generate instructions for causing the accurate robot to contact a fiducial associated with the patient, using the first registration.

Any of the aspects herein, wherein the memory stores further data for processing by the processor that, when processed, causes the processor to: generate instructions for guiding a navigated tool to contact a fiducial associated with the patient, using the second registration.

Any of the aspects herein, wherein the memory stores further data for processing by the processor that, when processed, causes the processor to: quantify an error between the first registration and the second registration; and generate an alert if the quantified error exceeds a predetermined threshold.

Any of the aspects herein, wherein the memory stores further data for processing by the processor that, when processed, causes the processor to: identify, when the quantified error exceeds a predetermined threshold, whether the quantified error is attributable to the first registration, the second registration, or a movement of the patient's anatomy.

Any of the aspects herein, wherein the memory stores further data for processing by the processor that, when processed, causes the processor to: verify an accuracy of the first registration or the second registration.

Any of the aspects herein, wherein the verifying comprises: determining whether the accurate robot, when positioned based on the first registration, and a navigated tool, when positioned based on the second registration, reach a predetermined position relative to the patient's anatomy.

Any of the aspects herein, wherein the verifying occurs automatically.

A system according to at least one embodiment of the present disclosure comprises an imaging device; a processor; and a memory storing data for processing by the processor that, when processed, causes the processor to: receive, from the imaging device, an image depicting a portion of a patient's anatomy and a tracking device affixed to an accurate robot, the tracking device having first markers visible in the image and second markers visible to a navigation system; correlate a robot coordinate system and a patient coordinate system, based on the image and a known pose of the accurate robot, to yield a first registration; correlate a navigation coordinate system and the patient coordinate system, based on a position of the second markers as detected by the navigation system and the image, to yield a second registration; and control one of the accurate robot and a navigated tool based on the first registration or the second registration, respectively.

Any of the aspects herein, wherein the memory stores further data for processing by the processor that, when processed, causes the processor to: detect an error in at least one of the first registration and the second registration; and identify whether the error is attributable to the first registration, the second registration, or a change in pose of the patient's anatomy.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Consolidation of different technologies in the same surgical system used for a surgical procedure is becoming more common, along with providing an improved accuracy that can enable or improve clinical sections of the procedure and its clinical outcomes. As more technologies are combined, a transformation chain (i.e., an amount of different coordinate systems combinations in a row needed from a patient anatomy to an operational tool or software) may decrease an accuracy of a registration (e.g., error may build up which each transformation change in a resulting coordinate system alignment). Hence, in general, more transformations in a transformation chain may cause the accuracy error to increase.

At least one embodiment according to the present disclosure enables two or more different registration paths in a single acquisition set to enable two separate correlations, which may provide at least two benefits. First, an accuracy of each of the paths may be improved. In a conventional path for a Mazor X Stealth Edition system, for example, correlating a patient anatomy to a robot system to a navigation system may result in an increased error for the navigation system as the navigation system's error is built on top of the robotic system. If the order is reversed (e.g., correlating a patient anatomy to a navigation system to a robot system), then the robot may have an increased error as the robot builds error on top of the navigation system. By enabling two separate registration paths, the errors may be decreased or eliminated as the patient anatomy is directly and independently correlated to the robotic system in addition to being directly and independently correlated to the navigation system. Second, the different registration processes may be used to verify each registration process and act as an additional safety or error reduction (by any type of error averaging).

At least one embodiment according to the present disclosure enables different systems to use the same acquisition set (e.g., an O-arm auto-registration may use an O-arm navigation tracker and at the same time a location of beads on a marker within the same image acquired may be analyzed (the beads may be, for example, a star marker or a SpineAir). The combination of the two registrations may be performed twice (e.g., for comparison reasons). First, using a transformation between the patient anatomy to the robot system to the navigation system may be performed and then a transformation between the patient anatomy to the navigation system to the robot system (in a different method) may be performed. Both transformations may be measured and compared to one other and may enable a user to use both navigation and robotics (in this example) each per its registration method (e.g., using the shorter transformation chain).

The present disclosure provides value at least by enabling more features to a user that may require higher safety factors.

Embodiments of the present disclosure provide technical solutions to one or more of the problems of (1) correlating multiple systems used for a surgical procedure, (2) decreasing registration accuracy errors, (3) validating one or more registration processes, and (4) increasing patient safety.

Figure 1:
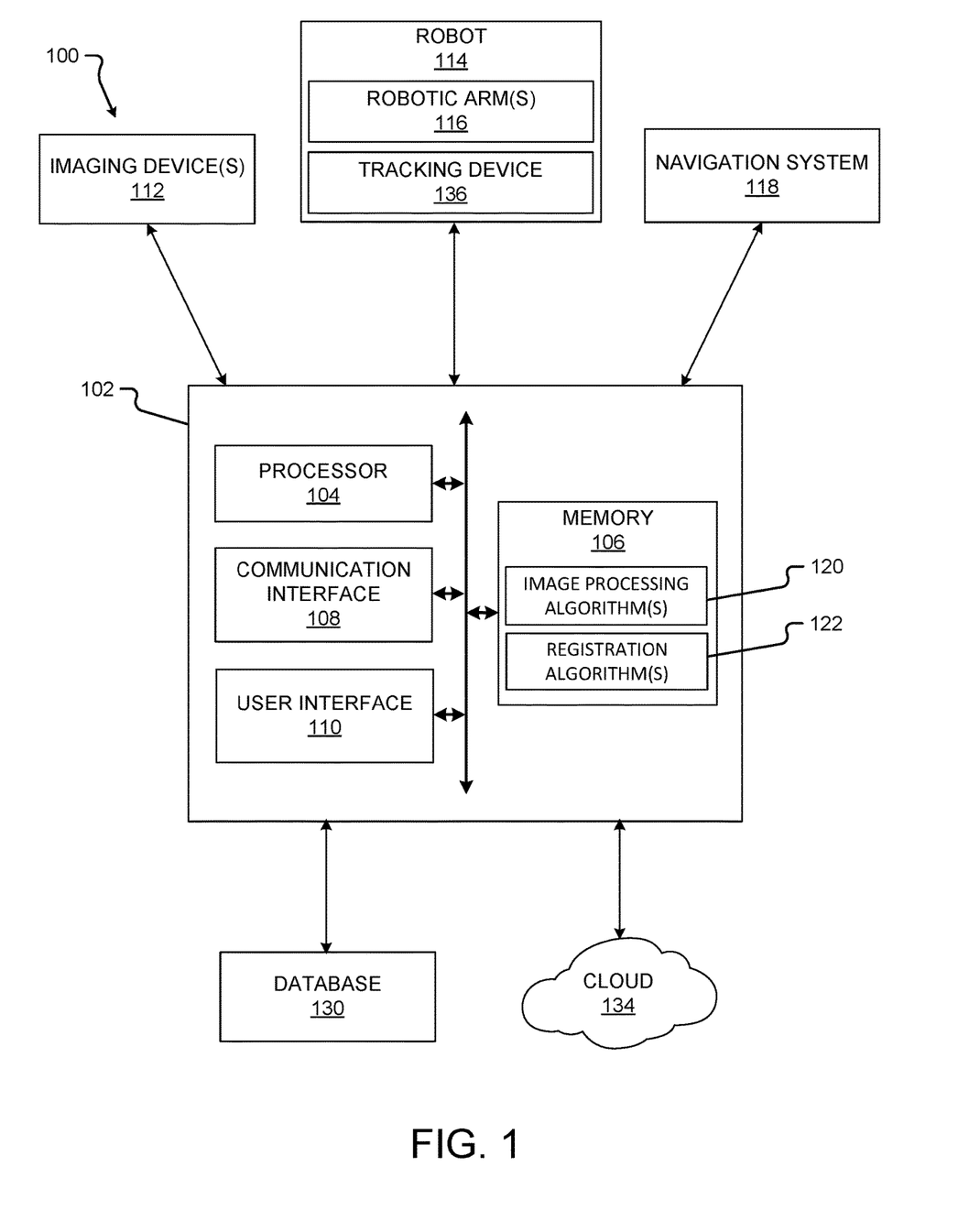
FIG. 1 is a block diagram of a system according to at least one embodiment of the present disclosure.

Turning first to FIG. 1, a block diagram of a system 100 according to at least one embodiment of the present disclosure is shown. The system 100 may be used to generate multiple registrations and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200, 300, 400, 500, 600, and/or 700 described herein, or of any other methods. The memory 106 may store, for example, one or more image processing algorithms 120 and/or one or more registration algorithms 122. Such instructions or algorithms may, in some embodiments, be organized into one or more applications, modules, packages, layers, or engines. Alternatively or additionally, the memory 106 may store other types of data (e.g., machine learning modes, artificial neural networks, etc.) that can be processed by the processor 104 to carry out the various method and features described herein. Thus, although various components of memory 106 are described as instructions, it should be appreciated that functionality described herein can be achieved through use of instructions, algorithms, and/or machine learning models. The data, algorithms and/or instructions may cause the processor 104 to manipulate or otherwise process data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, a series of images (e.g., video), and/or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, a tracking device 136 may be held by, placed on, affixed to, or otherwise secured to the robot 114 (including, e.g., on the robotic arm 116), the imaging device 112, or any other object in the surgical space. The tracking device 136 may comprise first reference markers (which may also be referred to herein simply as markers) configured to be detected and/or tracked by an imaging device such as the imaging device 112, and second reference markers configured to be detected and/or tracked by a navigation system such as the navigation system 118. For example, the tracking device may comprise metal balls that are detectable and/or trackable using an X-ray imaging device (including, for example, a C-arm, an O-arm, a fluoroscope), and infrared-reflecting spheres that are detectable and/or trackable by the navigation system 118 (including, for example, an infrared camera of the navigation system 118). The results of the tracking may be used by the robot 114, a computing device 102, any other component of the system 100, and/or by an operator of the system 100. In some embodiments, the navigation system 118 can be used to track components of the system other than the robot 114 (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The system 100 or similar systems may be used, for example, to carry out one or more aspects of any of the methods 200, 300, 400, 500, 600 and/or 700 described herein. The system 100 or similar systems may also be used for other purposes.

Figure 2:
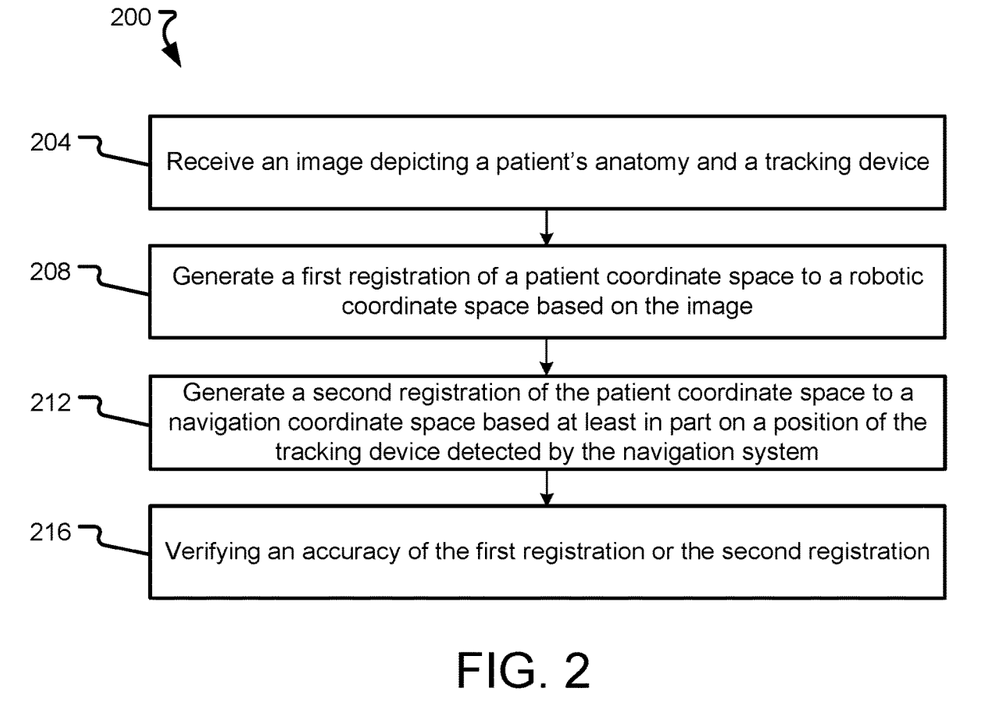
FIG. 2 is a flowchart according to at least one embodiment of the present disclosure.

FIG. 2 depicts a method 200 that may be used, for example, to generate two independent registrations, including, for example, one registration between a robotic coordinate system and a patient coordinate system, and another registration between a navigation coordinate system and the patient coordinate system.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as an image processing algorithm 120 and/or a registration algorithm 122.

The method 200 comprises receiving an image depicting a patient's anatomy and a tracking device (step 204). The image may be received via a user interface such as the user interface 110 and/or a communication interface such as the communication interface 108 of a computing device such as the computing device 102, and may be stored in a memory such as the memory 106 of the computing device. The image may also be received from an external database or image repository (e.g., a hospital image storage system, such as a picture archiving and communication system (PACS), a health information system (HIS), and/or another system for collecting, storing, managing, and/or transmitting electronic medical records including image data), and/or via the Internet or another network. In other embodiments, the image may be received or obtained from an imaging device such as the imaging device 112, which may be any imaging device such as an MRI scanner, a CT scanner, any other X-ray based imaging device, or an ultrasound imaging device. The image may also be generated by and/or uploaded to any other component of a system such as the system 100. In some embodiments, the image may be indirectly received via any other component of the system or a node of a network to which the system is connected.

The image may be a 2D image or a 3D image or a set of 2D and/or 3D images. In some embodiments, the image may be an X-ray image. The image may depict a patient's anatomy or portion thereof. In some embodiments, the image may be captured preoperatively (e.g., before surgery) and may be stored in a system (e.g., a system 100) and/or one or more components thereof (e.g., a database 130). The stored image may then be received (e.g., by a processor 104), as described above, preoperatively (e.g., before the surgery) and/or intraoperatively (e.g., during surgery).

In some embodiments, the image may depict an anatomical portion of a patient. In other embodiments, the image may depict multiple anatomical elements associated with the patient anatomy, including incidental anatomical elements (e.g., ribs or other anatomical objects on which a surgery or surgical procedure will not be performed) in addition to target anatomical elements (e.g., vertebrae or other anatomical objects on which a surgery or surgical procedure is to be performed). The image may comprise various features corresponding to the patient's anatomy and/or anatomical elements (and/or portions thereof), including gradients corresponding to boundaries and/or contours of the various depicted anatomical elements, varying levels of intensity corresponding to varying surface textures of the various depicted anatomical elements, combinations thereof, and/or the like. The image may depict any portion or part of patient anatomy and may include, but is in no way limited to, one or more vertebrae, ribs, lungs, soft tissues (e.g., skin, tendons, muscle fiber, etc.), a patella, a clavicle, a scapula, combinations thereof, and/or the like.

The image may also depict a tracking device such as the tracking device 136. In some embodiments, the tracking device may have first markers visible in the image and second markers visible to a navigation system such as the navigation system 118. For example, the tracking device may comprise metal balls that are detectable and/or trackable using an X-ray imaging device (including, for example, a C-arm, an O-arm, a fluoroscope), and infrared-reflecting spheres that are detectable and/or trackable by the navigation system (including, for example, an infrared camera of the navigation system). In some embodiments, the tracking device (and thus, in some instances, both the first markers and the second marker) may be affixed to a robotic arm such as the robotic arm 116 or to any portion of a robot such as the robot 114. The robot may be an accurate robot. For example, the robot may have sensors to yield sensor data including a pose of the robot or any portion of the robot thereof. In other embodiments, the first markers may be affixed to the robot and the second markers may be affixed to the patient. It will be appreciated that the tracking device may have any number of markers visible and any marker may be visible in the image and/or detectable by the navigation system.

Each image may be processed using an image processing algorithm such as the image processing algorithm 120 to identify anatomical elements and/or the tracking device in the image. In some embodiments, feature recognition may be used to identify a feature of the anatomical element or the tracking device. For example, a contour of a vertebrae, femur, or other bone may be identified in the image. In other embodiments, the image processing algorithm may use artificial intelligence or machine learning to identify the anatomical element and/or the tracking device. In such embodiments, a plurality of training images may be provided to a processor such as the processor 104, each training image annotated to include identifying information about a tracking device and/or an anatomical element in the image. The processor, executing instructions stored in memory such as the memory 106 or in another memory, may analyze the images using a machine-learning algorithm and, based on the analysis, generate one or more image processing algorithms such as the image processing algorithms 120 for identifying anatomical elements and/or objects such as the tracking device in an image.

The method 200 also comprises generating a first registration of a patient coordinate space to a robotic coordinate space based on the image (step 208). The image may be the image received in step 204. A processor such as the processor 104 may generate the first registration. Generating the first registration may utilize one or more registration algorithms, such as the registration algorithms 122. Generating the first registration may also be based on information about a pose of the robot (which may be obtained from, for example, sensors on the robot operable to generate sensor data about a pose of the robot). In some embodiments, generating the first registration may include correlating the patient coordinate space to the robotic coordinate space based on the tracking device depicted in the image and the pose of the robot. In such embodiments, because the tracking device is affixed to the robot (and more specifically, for example, the robotic arm) and a pose of the robot is known, a pose of the tracking device is also known. The known pose of the tracking device and the image depicting the tracking device may be used to generate the first registration. In other words, the processor may correlate the patient anatomy depicted in the image (and thus, the patient coordinate space) to the robot (and thus, the robotic coordinate space) based on the known pose of the tracking device depicted in the image.

The method 200 also comprises generating a second registration of the patient coordinate space to a navigation coordinate space based at least in part on a position of the tracking device detected by the navigation system (step 212). A processor such as the processor 104 may generate the second registration. Generating the second registration may utilize one or more registration algorithms, such as the registration algorithms 122. Generating the second registration may be based at least in part on a position of the second markers detected by the navigation system. A pose of the second markers (and thus, a pose of the tracking device) may be detectable by the navigation system. For example, the second markers may be infrared light emitting diodes (ILEDs) and the navigation system may include an infrared camera operable to detect the ILEDs. Generating the second registration may also be based on the image received in step 204. For example, a processor such as the processor 104 may correlate the patient anatomy depicted in the image (and thus, the patient coordinate space) to the navigation system based on the known pose of the tracking device depicted in the image.

It will be appreciated that the first registration generated in step 208 is independent of the second registration generated in step 212. By having independent registrations, various potential errors may be detected, for example, a robotic error may be detected by the navigation system.

The method 200 also comprises verifying an accuracy of the first registration or the second registration (step 216). A processor, such as the processor 104, may verify the accuracy of the first registration and/or the second registration. The accuracy of the first registration and/or the second registration may be verified automatically. In some instances, step 216 may automatically occur when steps 204-212 (in any order) are completed.

Verifying the accuracy of the first registration and/or the second registration may comprise causing the robot and/or a navigated tool, respectively, to contact a known point relative to the patient's anatomy. The known point relative to the patient's anatomy may be, in some examples, a point on an anatomical feature of the patient's anatomy. Verifying the accuracy may also comprise comparing the known point to a point as determined by a processor such as the processor 104 using the first registration and/or the second registration. For example, the known point may be a point on a vertebra. The known point on the vertebra as determined by the robot and/or the navigated tool may be compared to the point on the vertebra as determined based on the first registration and/or the second registration, respectively. A mismatch of the known point based on the robot and/or the navigated tool and the point based on the first registration and/or the second registration, respectively, may indicate that the first registration and/or the second registration may be inaccurate. A match of the known point based on the robot and/or the navigated tool and the point based on the first registration and/or the second registration may indicate that the first registration and/or the second registration, respectively is accurate.

In some embodiments, verifying the accuracy of the first registration and/or the second registration may comprise determining whether the robot, when positioned based on the first registration, and a navigated tool, when positioned based on the second registration, reach a predetermined position. The predetermined position may be relative to the patient's anatomy in some embodiments. In other embodiments, the predetermined position may be relative to any component of a system such as the system 100. The predetermined position may be determined automatically in some embodiments. For example, the processor may automatically select a position on the patient or a distinguishable position in the surgical room as the predetermined position. In other embodiments, the predetermined position may be or comprise, or be based on, surgeon input received via the user interface. In further embodiments, the predetermined position may be determined automatically by the processor, and may thereafter be reviewed and approved (or modified) by a surgeon or other user.

It will be appreciated that step 216 is an example step for verifying the accuracy of the first registration and/or the second registration. Methods 300, 400, 500, and 600 described below are also example methods for verifying the accuracy of the first and/or second registrations.

The present disclosure encompasses embodiments of the method 200 that comprise more or fewer steps than those described above, and/or one or more steps that are different than the steps described above.

Figure 3:
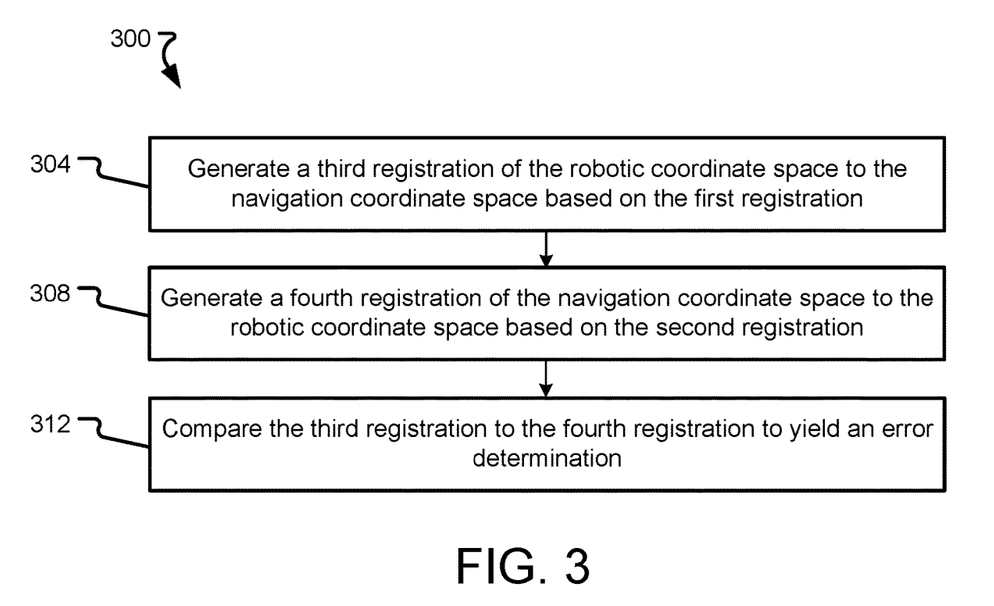
FIG. 3 is a flowchart according to at least one embodiment of the present disclosure.

FIG. 3 depicts a method 300 that may be used, for example, to verify an accuracy of the first and/or second registrations described above in connection with FIG. 2.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as an image processing algorithm 120 and/or a registration algorithm 122.

The method 300 comprises generating a third registration of the robotic coordinate space to the navigation coordinate space based on the first registration (step 304). Generating the third registration may utilize one or more registration algorithms, such as the registration algorithms 122. A processor such as the processor 104 may correlate the robotic coordinate space to the navigation coordinate space based on the first registration. As a result, the patient coordinate space will be correlated to the robotic space, which will be correlated to the navigation space.

The method 300 also comprises generating a fourth registration of the navigation coordinate space to the robotic coordinate space based on the second registration (step 308). Generating the fourth registration may utilize one or more registration algorithms, such as the registration algorithms 122. A processor such as the processor 104 may correlate the navigation coordinate space to the robotic coordinate space based on the second registration. As a result, the patient coordinate space will be correlated to the navigation space, which will be correlated to the robotic coordinate space.

The method 300 also comprises comparing the third registration to the fourth registration to yield an error determination (step 312). Comparing the third registration to the fourth registration may comprise determining a point by a processor such as the processor 104 using the third registration and determining the point by the processor using the fourth registration. The point based on the third registration may be compared to the point based on the fourth registration to yield the error determination. A mismatch of the point based on the third registration and the point based on the fourth registration may indicate that an error has occurred and that the first registration and/or the second registration may be inaccurate. A match of the point based on the third registration and the point based on the fourth registration may indicate that an error has not occurred and that the first registration and/or the second registration is accurate.

The present disclosure encompasses embodiments of the method 300 that comprise more or fewer steps than those described above, and/or one or more steps that are different than the steps described above.

Figure 4:
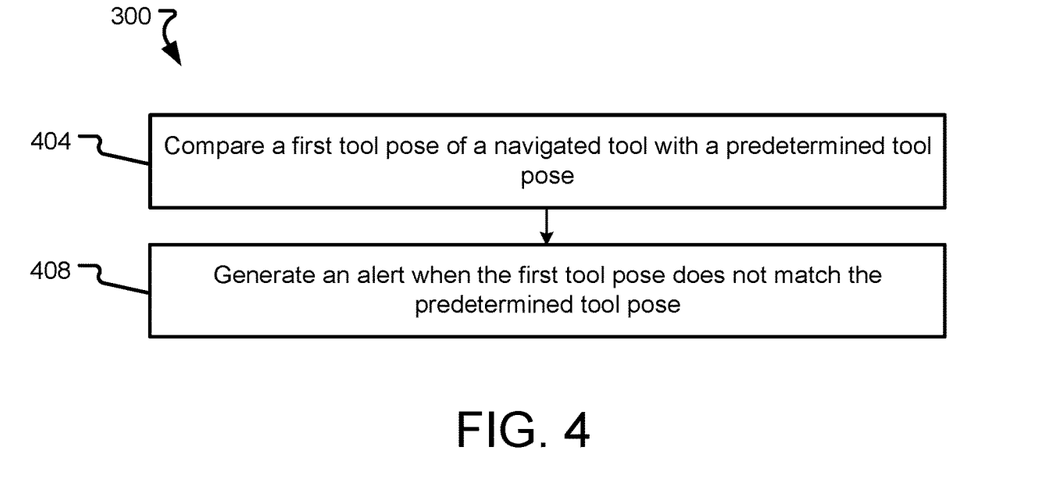
FIG. 4 is a flowchart according to at least one embodiment of the present disclosure.

FIG. 4 depicts a method 400 that may be used, for example, to verify an accuracy of the first and second registrations described above in connection with FIG. 2.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120 and/or a registration algorithm 122.

The method 400 comprises comparing a first tool pose of a navigated tool with a predetermined tool pose (step 404). The first tool pose may be determined by a navigation system such as the navigation system 118 detecting, for example, a tracking device such as the tracking device 136 affixed to the navigated tool.

In some embodiments, the navigated tool may be at least partially supported and/or oriented by a robot, such as the robot 114, and more specifically, may be supported and/or oriented by a robotic arm such as the robotic arm 116 of the robot. The robot may be an accurate robot in which sensors on the robot may yield sensor data including a pose of the robot or any portion of the robot thereof. In other embodiments, the navigated tool may be affixed to any portion of the robot 114. In such embodiments where the navigated tool is supported or oriented by the robot or robotic arm, the predetermined tool pose may be determined from the robot.

In still other embodiments, the navigated tool may be affixed to any component of a system such as the system 100 or the patient. In such embodiments, determining the predetermined tool pose may comprise causing the robot, respectively, to contact the navigated tool. A pose of the robot when the robot is contacting the navigated tool may be obtained from the robot and the pose of the robot may correlate to a pose of the navigated tool. Thus, the predetermined tool pose may be based on the pose of the robot when the robot contacts the navigated tool.

The method 400 also comprises generating an alert when the first tool pose does not match the predetermined tool pose (step 408). The alert may be a visual alert, an audible alert, or any type of alert communicated to a user. The alert may be communicated to the user via a user interface such as the user interface 110. In some embodiments, the alert may be automatically generated by the processor 104. In other embodiments, the alert may be automatically generated by any component of a system such as the system 100.

In some embodiments, the alert may simply notify a surgeon or other medical provider that the first tool pose does not match the predetermined tool pose. In other embodiments, the alert may prompt the surgeon or other medical provider to re-generate the first registration and/or the second registration and may require the surgeon or other medical provider to confirm such re-generation. The alert may also cause the method 400, or any verification step (e.g., step 216, methods 300, 500, or 600) to be repeated to confirm accuracy of the regenerated first registration and/or the second registration.

The present disclosure encompasses embodiments of the method 400 that comprise more or fewer steps than those described above, and/or one or more steps that are different than the steps described above.

Figure 5:
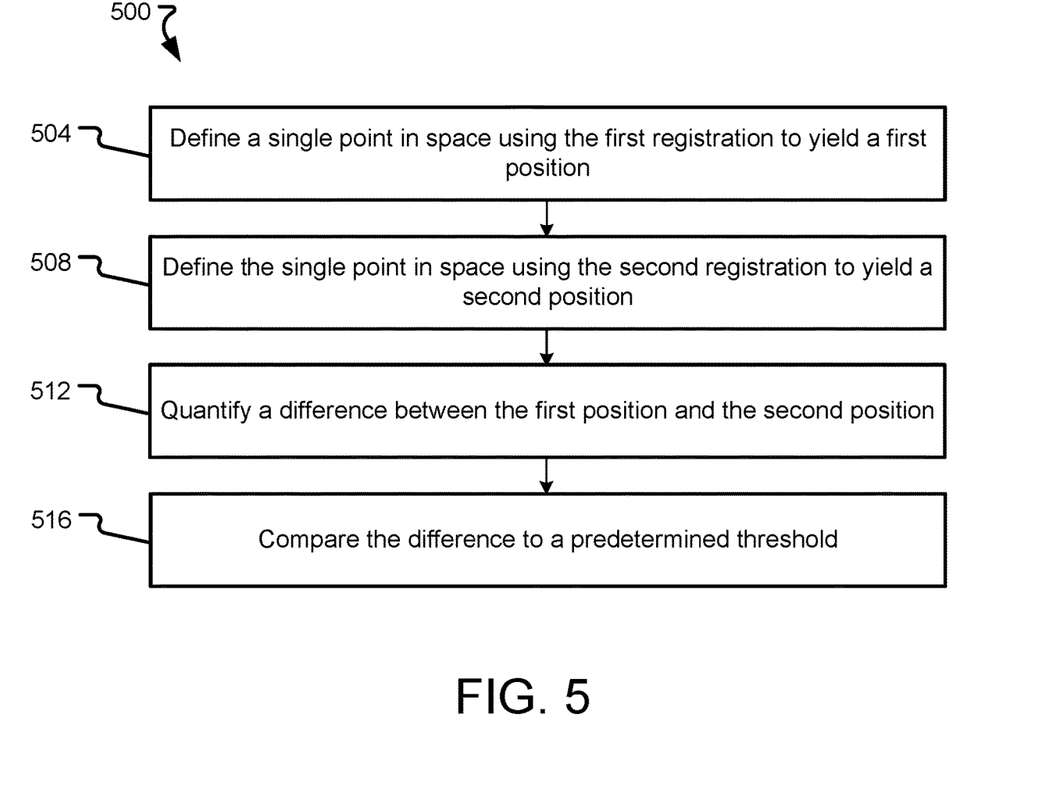
FIG. 5 is a flowchart according to at least one embodiment of the present disclosure.

FIG. 5 depicts a method 500 that may be used, for example, to verify an accuracy of the first and second registrations described above in connection with FIG. 2.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as an image processing algorithm 120 and/or a registration algorithm 122.

The method 500 comprises defining a single point in space using the first registration to yield a first position (step 504). A processor such as the processor 104 may be used to define the single point to yield the first position. The first position may be relative to the patient's anatomy. For example, the first point may be, in some examples, a point on an anatomical feature of the patient's anatomy. In other instances, the first point may be relative to a robot such as the robot 114. For example, the first point may be an end effector or a tool supported by a robotic arm such as the robotic arm 116 of the robot. In other embodiments, the first point may be relative to any component, instrument, or tool of a system such as the system 100 or a patient.

The method 500 also comprises defining the single point in space using the second registration to yield a second position (step 508). The step 508 may be the same as or similar to the step 504 described above, except for the second registration is used to yield the second position.

The method 500 also comprises quantifying a difference between the first position and the second position (step 512). A processor such as the processor 104 may be used to quantify the difference between the first position and the second position. The processor may simply subtract an x and/or y coordinate of the first position from an x and/or y coordinate of the second position to determine the difference. In some embodiments, the difference may be tracked over time to detect and alert for changes that may have occurred in a pose or position of, for example, the robot, the patient, a device, an instrument, and/or a tool.

In other embodiments, a position or a pose of a tracked device as determined using a registration generated by correlating a navigation coordinate space to a robotic coordinate space to a patient coordinate space may be compared to a position or a pose of the tracked device as determined using a registration generating by correlating a navigation coordinate space to a patient coordinate space. The comparison may correlate to the difference. In at least some of the embodiments, the tracked device may be tracked by a navigation system such as the navigation system 118.

The method 500 also comprises comparing the difference to a predetermined threshold (step 516). A processor such as the processor 104 may be used to compare the difference quantified in step 512 to the predetermined threshold. The predetermined threshold may correlate to an acceptable difference between the first position and the second position that may be, for example, clinically irrelevant.

The predetermined threshold may be determined automatically using artificial intelligence and training data (e.g., historical cases) in some embodiments. In other embodiments, the predetermined threshold may be or comprise, or be based on, surgeon input received via the user interface. In further embodiments, the predetermined threshold may be determined automatically using artificial intelligence, and may thereafter be reviewed and approved (or modified) by a surgeon or other user.

The present disclosure encompasses embodiments of the method 500 that comprise more or fewer steps than those described above, and/or one or more steps that are different than the steps described above.

Figure 6:
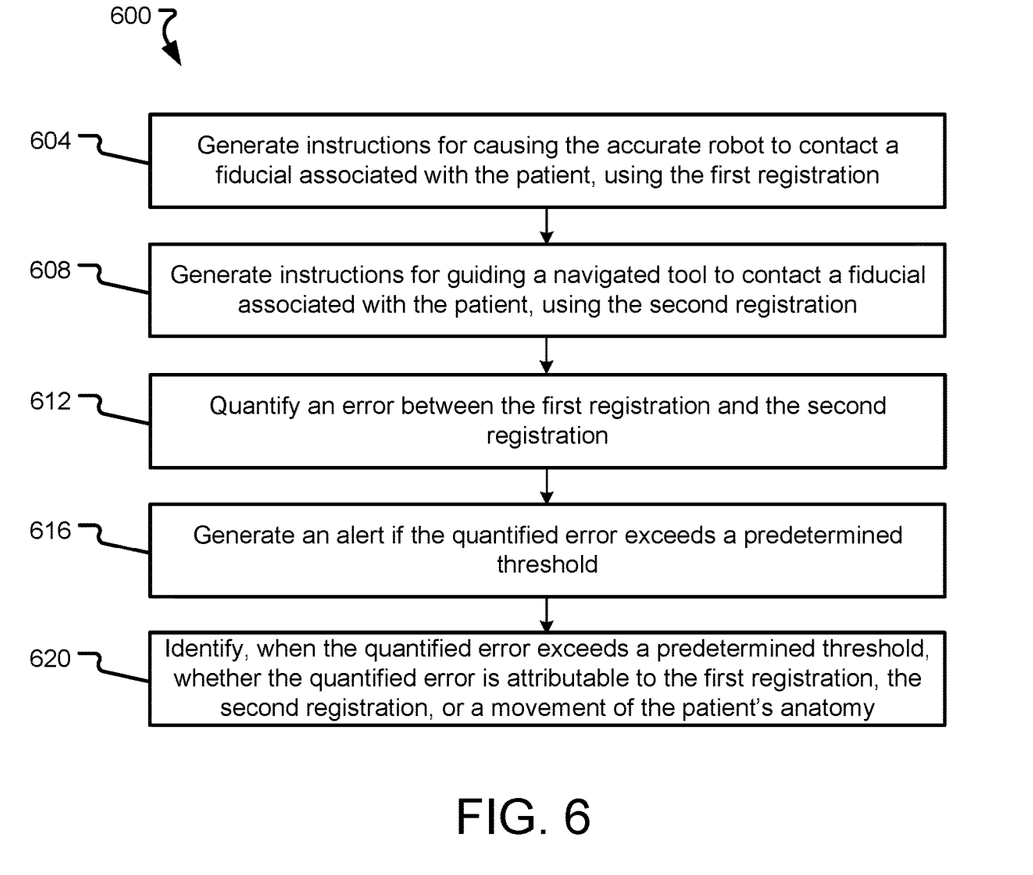
FIG. 6 is a flowchart according to at least one embodiment of the present disclosure.

FIG. 6 depicts a method 600 that may be used, for example, to verify an accuracy of the first and second registrations described above in connection with FIG. 2.

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 600. The at least one processor may perform the method 600 by executing instructions stored in a memory such as the memory 106. The instructions may correspond to one or more steps of the method 600 described below. The instructions may cause the processor to execute one or more algorithms, such as an image processing algorithm 120 and/or a registration algorithm 122.

The method 600 comprises generating instructions for causing an accurate robot to contact a fiducial associated with a patient, using a first registration (step 604). The first registration may be the same as or similar to the first registration generated in step 208 of method 200. The robot may be the same as or similar to the robot 114. The instructions may be generated automatically by, for example, a processor such as the processor 104. In some embodiments, the fiducial may be a tracking device such as the tracking device 136. In other embodiments, the fiducial may simply be a component such as, for example, a tool or instrument, of a system such as the system 100. The fiducial may be attached to the patient in some embodiments, and may not be attached to the patient in other embodiments. For example, the fiducial may be attached to an operating bed supporting the patient. In another example, the fiducial may be attached directly to a bone of the patient.

Causing the robot to contact the fiducial may include determining a position of the robot when the robot is contacting the fiducial. The robot may, for example, have sensors that may yield sensor data having information about a pose (e.g., positions and orientation) of the robot.

The method 600 also comprises generating instructions for guiding a navigated tool to contact a fiducial associated with the patient, using the second registration (step 608). The second registration may be the same as or similar to the second registration generated in step 212 of method 200. The instructions may be generated automatically by, for example, a processor such as the processor 104. The step 608 may be the same as or similar to step 604 with respect to the fiducial. Further, the fiducial contacted by the navigated tool may be the same as the fiducial contacted by the accurate robot in step 604. In other instances, the fiducial contacted may be a different fiducial contacted by the accurate robot in step 604.

Causing the navigated tool to contact the fiducial may include determining a position of navigated tool when the tool is contacting the fiducial. The position of the navigated tool can be obtained from a navigation system such as the navigation system 118 (for example, the navigation system may have a camera that can detect and track a tracking device such as the tracking device 136 affixed to the navigated tool).

The method 600 also comprises quantifying an error between the first registration and the second registration (step 612). The error may be automatically quantified by, for example, a processor such as the processor 104. Quantifying the error between the first registration and the second registration may include comparing the position of the robot when the robot contacts the fiducial in step 604 to the position of the navigated tool when the navigation tool contacts the fiducial in step 608. In some embodiments, the error may be based on a difference between the position of the robot when the robot contacts the fiducial and the position of the navigated tool when the navigated tool contacts the fiducial. In other embodiments, the error may be based on a difference between a position of the robot or the navigated tool and a predetermined position correlating to the fiducial.

The method 600 also comprises generating an alert if the quantified error exceeds a predetermined threshold (step 616). The step 616 may be the same as or similar to the step 408 of method 400 with respect to generating an alert. The step 616 may also be the same as or similar to the step 516 with respect to a predetermined threshold.

In some embodiments, the alert may simply notify a surgeon or other medical provider that the quantified error exceeds the predetermined threshold. In other embodiments, the alert may prompt the surgeon or other medical provider to re-generate the first registration and/or the second registration and may require the surgeon or other medical provider to confirm such re-generation. The alert may also cause the method 600, or any verification step (e.g., step 216, methods 400, 300, or 500) to be repeated to confirm accuracy of the first registration and/or the second registration.

The method 600 also comprises identifying, when the quantified error exceeds a predetermined threshold, whether the quantified error is attributable to the first registration, the second registration, or a movement of the patient's anatomy (step 620). For example, the instructions for causing the accurate robot to contact the fiducial as described in step 604 may include determining a predetermined position correlating to a position of the fiducial for the robot to orient to. Once the robot has moved to the predetermined position, a pose of the robot as determined from the robot can be compared to the predetermined position. If the pose of the robot is different from the predetermined position, than the quantified error may be attributable to the first registration.

In another example, the instructions for causing the navigated tool to contact the fiducial as described in step 608 may include a predetermined position correlating to a position of the fiducial for the navigated tool to move to. Once the navigated tool has moved to the predetermined position, a position of the tool as determined from the navigated system can be compared to the predetermined position. If the pose of the navigated tool is different from the predetermined position, than the quantified error may be attributable to the second registration.

In another example, a tracking device such as the tracking device 136 may be disposed on a patient and a camera of the navigation system may be positioned to obtain information about the tracking device incrementally or continuously. A processor such as the processor 104 may detect movement of the tracking device based on the information obtained from the camera. In some embodiments, the processor may compare a position of the tracking device in a first instance to a second instance. Movement of the tracking device may indicate that the quantified error is attributable to movement of the patient.

The present disclosure encompasses embodiments of the method 600 that comprise more or fewer steps than those described above, and/or one or more steps that are different than the steps described above.

Figure 7:
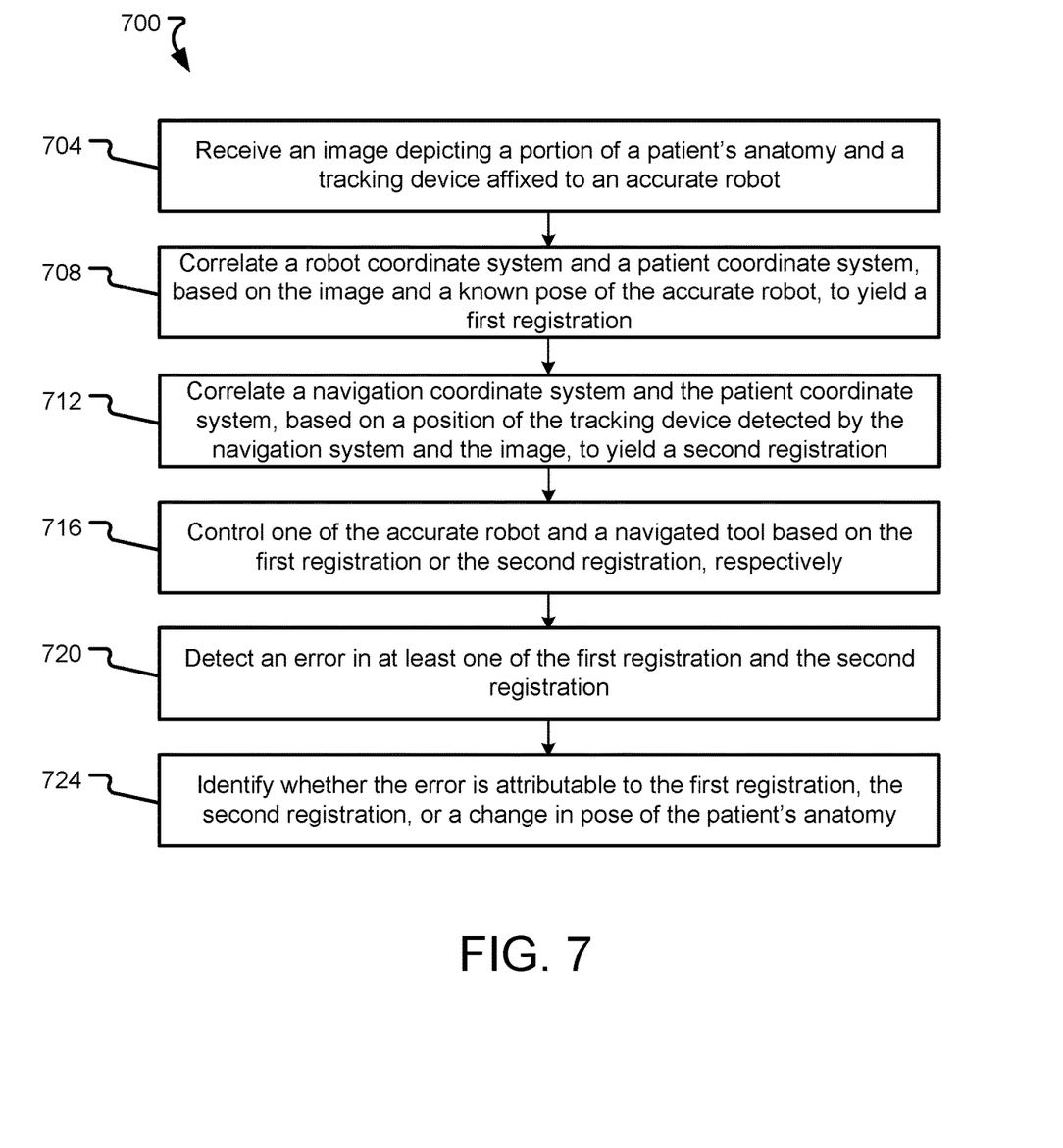
FIG. 7 is a flowchart according to at least one embodiment of the present disclosure.

FIG. 7 depicts a method 700 that may be used, for example, to generate two independent registrations using a single acquisition set.

The method 700 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 700. The at least one processor may perform the method 700 by executing instructions stored in a memory such as the memory 106. The instructions may correspond to one or more steps of the method 700 described below. The instructions may cause the processor to execute one or more algorithms, such as an image processing algorithm 120 and/or a registration algorithm 122.

The method 700 comprises receiving an image depicting a portion of a patient's anatomy and a tracking device affixed to an accurate robot (step 704). The step 704 may be the same as or similar to the step 204 of method 200 described above.

The method 700 also comprises correlating a robot coordinate system and a patient coordinate system, based on the image and a known pose of the accurate robot, to yield a first registration (step 708). The step 708 may be the same as or similar to the step 208 of method 200 described above.

The method 700 also comprises correlating a navigation coordinate system and the patient coordinate system, based on a position of the tracking device detected by the navigation system and the image, to yield a second registration (step 712). The step 712 may be the same as or similar to the step 212 of method 200 described above.

The method 700 also comprises controlling one of the accurate robot and a navigated tool based on the first registration or the second registration, respectively (step 716). For example, instructions may be generated by a processor, such as the processor 104, based on the first registration to cause the robot to move to a position and/or to orient and/or operate a tool or instrument. Instructions may also be generated based on the second registration to cause the navigated tool to be moved to a position or to perform a procedure. In some embodiments, the navigated tool may be oriented by the robot or by a different robot and the instructions may cause the robot (or the different robot) to orient the navigated tool to a position.

The method 700 also comprises detecting an error in at least one of the first registration and the second registration (step 720). The step 720 may be the same as or similar to step 612 of method 600. In some embodiments, the error may be detected by a navigation system such as the navigation system 118 monitoring a tracking device such as the tracking device 136 affixed or otherwise disposed on a robot such as the robot 114. A pose of the tracking device may be obtained from the robot (and more specifically a pose of the robot is obtained from, for example, sensors disposed or integrated with the robot and operable to yield sensor data containing information about a pose of the robot) and a pose of the tracking device may be determined by the navigation system. A mismatch between the pose of the tracking device as obtained from the robot and determined by the navigation system may indicate an error in at least one of the first registration and the second registration.

It will be appreciated that the step 720 may also incorporate steps from methods 200, 300, 400, 500, or 600 with respect to verifying the accuracy of the first registration and/or the second registration. When the first registration and/or the second registration are found to be inaccurate, this may indicate that an error in at least one of the first registration and the second registration has occurred.

The method 700 also comprises identifying whether the error is attributable to the first registration, the second registration, or a change in pose of the patient's anatomy (step 724). The step 724 may be the same as or similar to the step 620 of method 600 described above.

The present disclosure encompasses embodiments of the method 700 that comprise more or fewer steps than those described above, and/or one or more steps that are different than the steps described above.

As noted above, the present disclosure encompasses methods with fewer than all of the steps identified in FIGS. 2, 3, 4, 5, 6, and 7 (and the corresponding description of the methods 200, 300, 400, 500, 600, and 700), as well as methods that include additional steps beyond those identified in FIGS. 2, 3, 4, 5, 6, and 7 (and the corresponding description of the methods 200, 300, 400, 500, 600, and 700). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A dual registration method comprising:
receiving an image depicting a portion of a patient's anatomy and a tracking device affixed to an accurate robot, the tracking device having first markers visible in the image and second markers visible to a navigation system;

generating a first registration of a patient coordinate space to a robotic coordinate space based on the image;
generating a second registration of the patient coordinate space to a navigation coordinate space based at least in part on a position of the second markers detected by the navigation system;
comparing a first tool pose of a navigated tool with a predetermined tool pose, the first tool pose detected by the navigation system while the navigated tool is at least partially supported by the accurate robot; and
generating an alert when the first tool pose does not match the predetermined tool pose,
wherein the first registration and the second registration are independent of each other.

2. The method of claim 1, wherein the first registration is also based on information about a pose of the accurate robot in the image.

3. The method of claim 1, wherein the image is an X-ray image.

4. The method of claim 1, further comprising generating a third registration of the robotic coordinate space to the navigation coordinate space based on the first registration.

5. The method of claim 4, further comprising generating a fourth registration of the navigation coordinate space to the robotic coordinate space based on the second registration.

6. The method of claim 5, further comprising comparing the third registration to the fourth registration to yield an error determination.

7. The method of claim 1, further comprising verifying an accuracy of the first registration or the second registration by causing the accurate robot or a navigated tool, respectively, to contact a known point relative to the patient's anatomy.

8. The method of claim 7, wherein the known point relative to the patient's anatomy is a point on an anatomical feature of the patient's anatomy.

9. The method of claim 1, further comprising:
defining a single point in space using the first registration to yield a first position;
defining the single point in space using the second registration to yield a second position;
quantifying a difference between the first position and the second position; and
comparing the difference to a predetermined threshold.

10. A system for generating registrations, the system comprising:
a tracking device affixed to an accurate robot, the tracking device comprising first markers visible to an imaging device and second markers visible to a navigation system;
a processor; and
a memory storing data for processing by the processor, the data, when processed, causing the processor to:
register a patient coordinate system to a robotic coordinate system, based on an image depicting an anatomical portion of a patient and the tracking device, to yield a first registration;
register the patient coordinate system to a navigation coordinate system, based at least in part on a position of the second markers detected by the navigation system, to yield a second registration; and
generate instructions for causing the accurate robot to contact a fiducial associated with the patient, using the first registration,
wherein the first registration and the second registration are independent of each other.

11. The system of claim 10, wherein the memory stores further data for processing by the processor that, when processed, causes the processor to:
generate instructions for guiding a navigated tool to contact a fiducial associated with the patient, using the second registration.

12. The system of claim 10, wherein the memory stores further data for processing by the processor that, when processed, causes the processor to:
quantify an error between the first registration and the second registration; and
generate an alert if the quantified error exceeds a predetermined threshold.

13. The system of claim 12, wherein the memory stores further data for processing by the processor that, when processed, causes the processor to:
identify, when the quantified error exceeds a predetermined threshold, whether the quantified error is attributable to the first registration, the second registration, or a movement of the patient's anatomy.

14. The system of claim 10, wherein the memory stores further data for processing by the processor that, when processed, causes the processor to:
verify an accuracy of the first registration or the second registration.

15. The system of claim 14, wherein the verifying comprises:
determining whether the accurate robot, when positioned based on the first registration, and a navigated tool, when positioned based on the second registration, reach a predetermined position relative to the patient's anatomy.

16. The system of claim 14, wherein the verifying occurs automatically.

17. A system comprising:
an imaging device;
a processor; and
a memory storing data for processing by the processor that, when processed, causes the processor to:
receive, from the imaging device, an image depicting a portion of a patient's anatomy and a tracking device affixed to an accurate robot, the tracking device having first markers visible in the image and second markers visible to a navigation system;
correlate a robot coordinate system and a patient coordinate system, based on the image and a known pose of the accurate robot, to yield a first registration;
correlate a navigation coordinate system and the patient coordinate system, based on a position of the second markers as detected by the navigation system and the image, to yield a second registration;
control one of the accurate robot and a navigated tool based on the first registration or the second registration, respectively;
detect an error in at least one of the first registration and the second registration; and
identify whether the error is attributable to the first registration, the second registration, or a change in pose of the patient's anatomy.

* * * * *